(12) United States Patent
Sanfilippo et al.

(10) Patent No.: US 7,379,768 B2
(45) Date of Patent: May 27, 2008

(54) MEDICAL ELECTRODE AND METHOD OF USE

(76) Inventors: Robert Michael Sanfilippo, 890 Calle La Primavera, Glendale, CA (US) 91208; Rose Ann Yslas, 1828 Wollam St., Los Angeles, CA (US) 90065

(*) Notice: Subject to any disclaimer, the term of this patent is extended or adjusted under 35 U.S.C. 154(b) by 0 days.

(21) Appl. No.: 11/901,837

(22) Filed: Sep. 18, 2007

(65) Prior Publication Data
US 2008/0015426 A1    Jan. 17, 2008

Related U.S. Application Data

(63) Continuation-in-part of application No. 11/205,894, filed on Aug. 16, 2005.

(51) Int. Cl.
*A61B 5/04* (2006.01)

(52) U.S. Cl. ....................................... 600/391

(58) Field of Classification Search ................ 600/391, 600/392
See application file for complete search history.

(56) References Cited

U.S. PATENT DOCUMENTS

| 5,626,135 A | 5/1997 | Sanfilippo |
| 7,164,939 B2 | 1/2007 | LeSourd |

*Primary Examiner*—Lee S Cohen
(74) *Attorney, Agent, or Firm*—Gene Scott; Patent Law Group & Venture Group

(57) ABSTRACT

A medical electrode is made up of an insulating adhesive layer and an electrically conducting contact layer secured in a frictionally abutting relationship on an electrical terminal such that the contact layer is independently rotatable about the terminal. The contact layer provides an electrically conductive surface enabled for establishing common potential simultaneously with at least one removable electrode and the terminal. The terminal provides a base portion positioned for electrical contact with a skin surface when the adhesive layer is adhered to the skin surface.

8 Claims, 2 Drawing Sheets

MEDICAL ELECTRODE AND METHOD OF USE

CROSS-REFERENCE TO RELATED APPLICATIONS

Figure 1:
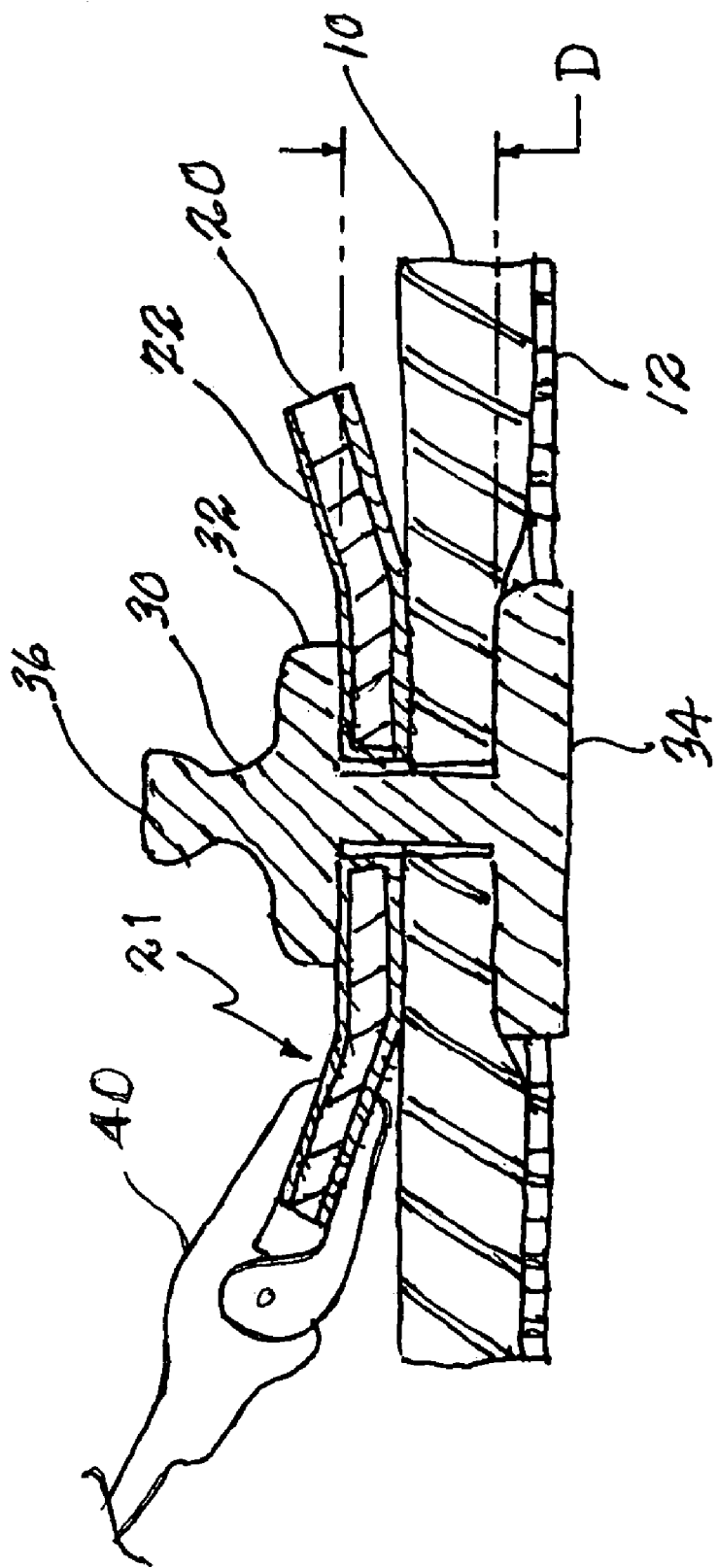

This is a continuation-in-part application of U.S. patent application Ser. No. 11/205,894, filed Aug. 16, 2005, now pending, and which is incorporated herein by reference.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

REFERENCE TO A "MICROFICHE APPENDIX"

Not applicable.

BACKGROUND OF THE INVENTION

1. Field of the Present Disclosure

This disclosure relates generally to medical devices and more particularly to a medical electrode with plural connection points for attachment of several monitoring devices simultaneously.

2. Description of Related Art Including Information Disclosed under 37 CFR 1.97 and 1.98

Medical electrodes are utilized in a number of applications for a variety of diagnostic and monitoring purposes. For instance, electrodes commonly are used to monitor physiological electric potentials to detect muscular activity of a person's heart. The cardiovascular activity of the heart is typically monitored by adhering or connecting electrodes to the skin of the patient at particular locations of interest on the body. The electrodes are then electrically coupled to electrical equipment such as an electrocardiograph (also referred to as EKG) apparatus that monitors the muscular activity of the heart. The resulting traces or output of the EKG provides a diagnostic tool for detecting heart disease and/or heart dysfunction of various etiology.

Applicant's prior patent, U.S. Pat. No. 5,626,135 describes the uses of medical electrodes and applications in the prior art quite thoroughly. U.S. Pat. No. 5,626,135 is hereby incorporated into the present application by reference.

LeSourd, U.S. Pat. No. 7,164,939 extends the concept of U.S. Pat. No. 5,626,135 to the usage of plural tabs.

The prior art does not teach the construction of a medical electrode with plural tabs wherein the electrode with tabs is able to be rotated to provide the ability to attach clip- on wires in a more convenient manner that may be advantageous in preventing wire tangles.

BRIEF SUMMARY OF THE INVENTION

A need exists for a medical electrode to which several electrical instruments can be simultaneously attached so as to monitor physiological electrical potentials at a specific location on a patient's skin surface. In accordance with one aspect of the present medical electrode an electrically conductive layer has a centrally positioned terminal and a plurality of tab portions peripheral thereto. An insulation layer is mounted to the skin of the patient and the electrically conductive layer is mounted on top of it. The conductive layer provides a conductive surface for electrically interconnecting a plurality of clip electrodes to the central terminal which is able to then make electrical contact with a primary monitoring equipment via a snap-on connector, and also to the skin of the patent via a conductive gel or similar substance between the central terminal and the patient's skin. In accordance with additional aspects of the present invention, a medical electrode is provided for simultaneous use with a primary electrical instrument and a plurality of auxiliary electrical instruments. The medical electrode includes an electrically conductive contact layer which supports an electrically conductive terminal. The terminal includes an engagement end, which is distal to the base. Plural electrically conductive tabs of the medical electrode are in electrical common with the terminal and the skin of the patient. The electrically conductive layer is able to be rotated so that a free tab can be positioned for each new conductor.

One object of the present apparatus is to provide benefits and improvements not known in prior art devices.

A further objective is to provide such an apparatus that is able to connect a plurality of monitoring devices to a single area of a patent's skin surface for electrical contact.

A still further objective is to provide such an apparatus that is able to provide electrical contact to plural electrical clips without physical interference with a central snap-on type terminal connector.

A still further objective is to provide such an apparatus that is easy to apply and remove, is inexpensive to manufacture and has a long shelf life.

A yet still further objective is to provide such an apparatus that is able to rotate to accept each new clip in a convenient manner and to avoid wire tangles.

BRIEF DESCRIPTION OF THE SEVERAL VIEWS OF THE DRAWING(S)

Figure 2:
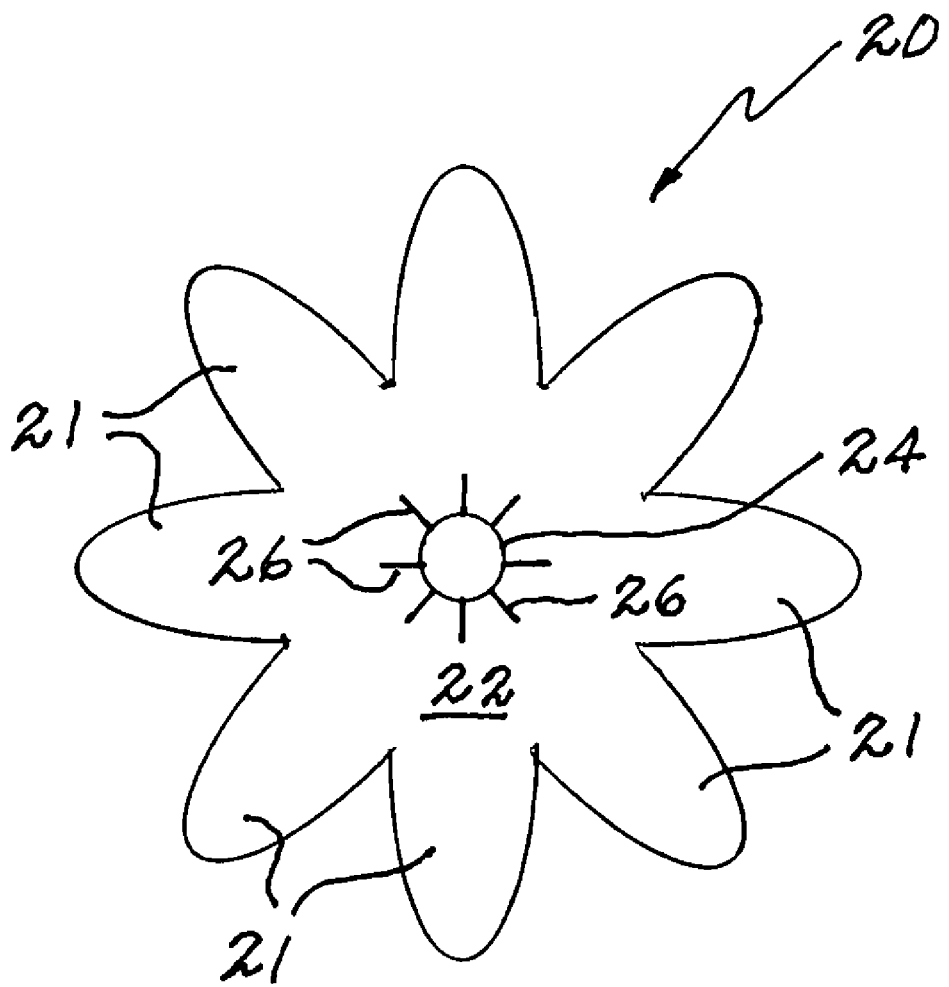

These and other features of the invention will now be described with reference to the drawings of preferred embodiments which are intended to illustrate and not to limit the invention, and in which:

FIG. 1 is a vertical cross-sectional view of a medical electrode in accordance with a preferred embodiment of the present invention; and FIG. 2 is a plan view of a contact layer thereof.

DETAILED DESCRIPTION OF THE INVENTION

The above described drawing figures illustrate the described apparatus and its method of use in at least one of its preferred, best mode embodiments, which is further defined in detail in the following description. Those having ordinary skill in the art may be able to make alterations and modifications to what is described herein without departing from its spirit and scope. Therefore, it should be understood that what is illustrated is set forth only for the purposes of example and that it should not be taken as a limitation in the scope of the present apparatus and method of use.

The apparatus described and claimed herein is a medical electrode for simultaneous use with a primary electrical monitoring instrument such as an EKG machine, and one or more auxiliary electrical instruments. The medical electrode, as shown in cross-section in FIG. 1, comprises an insulating adhesive layer 10 and an electrically conducting contact layer 20 both secured in a frictionally abutting relationship on an electrical terminal 30 such that the layers 10, 20 are independently rotatable about the terminal 30. Terminal 30 is preferably a metal part with good electrical conduction properties, as for instance made of aluminum or copper. The contact layer 20 provides an electrically conductive surface 22 enabled for establishing a common electrical potential simultaneously between at least one removable electrode 40, such as an alligator clip, and the terminal 30. Both the degree of frictional resistance to rotation between abutting layers 10, and 20; as well as the quality of electrical continuity (conductivity) between conductive surface 22 and terminal 30 are both established by the compressive pressure on contact layer 20, and this is related to the spacing between flange 32 and base 34, shown by letter "D" in FIG. 1, as well as the thicknesses of layers 10 and 20 and the resilience of adhesive layer 10. The total thickness of layers 10 and 20 and the compressive resilience of adhesive layer 10 may be selectively chosen to achieve a desired contact force between conduct layer 20 and flange 32.

In order to assemble contact layer 20, see FIG. 2, onto terminal 30, a central clearance hole 24 is formed in layer 20 and radial cuts 26 are made so that layer 20 is able to be pressed onto terminal 30 over flange 32 while still allowing layer 20 to resume its planar conformation after assembly as shown in FIG. 1. To accomplish this, clearly the material of layer 20 must be flexible but also somewhat stiff so as to resume its planar shape after deformation during assembly.

Layer 10 is made of a highly flexible and resilient material which is able to be stretched over flange 32 for assembly. The degree of rotational resistance of layer 20 is preferably set so that contact layer 20 is able to be manually rotated about terminal 30 and yet will not rotate under the typically forces exerted by wired connections attached to its protruding lobes 21 (FIG. 2). It is undesirable to allow such forces to rotate layer 10 which would move the positions of the connecting wires as this could interfere with medical operations and procedures. The degree of tightness and compression of layers 10 and 20 is partly dependent also on the degree of compression of adhesive layer 10 due to its resilient force. It is desired, upon assembly of layers 10 and 20 to be able to manually rotate layer 20 about terminal 30 but to prevent it from such rotation otherwise during use.

Preferably, the adhesive layer 10 is formed from a flexible and resilient sheet stock of foam material having an adhesive coating 12 on one side thereof as shown in FIG. 1 and preferably, this coating 12 is peripheral to base 34. Preferably, the contact layer 20 is formed from a flexible but relatively stiff sheet stock made of any single material or combination of materials such as paper, cardboard, and plastic.

As shown in FIG. 1, base 34 is positioned for electrical contact with a skin surface (not shown) when the adhesive coating 12 on layer 10 is adhered to the skin surface.

Preferably, the contact layer 20 is formed with a plurality of individual lobes or contact tabs 21 which are similar to those shown as numeral 29 in FIG. 3 of incorporated parent application Ser. No. 11205894. Preferably, the conductive surface 22 may be applied to layer 20 as an adhering metallized layer, a bonded metal foil layer, or a metal electrodeposited layer, and may cover only the surface of layer 20 that faces flange 32, or it may be also continuous in hole 24, or it may cover all surfaces of contact layer 20. The purpose here is to achieve electrical continuity while retaining a stiff but flexible substrate property because it is desirable to have the contact tabs 21 slightly bent away from layer 10, as shown in FIG. 1, so that electrodes 40 are more easily attached thereto.

Preferably, terminal 30 provides a central male receiver 36 for a snap-on female electrode. Such snap-action type terminals are well known in the prior art and are described in the incorporated reference, U.S. Pat. No. 5,626,135. With the presently described medical electrode attached to a skin surface, the receiver 36 is positioned and oriented for being engaged by female snap-on electrode so as to connect an electrical device such as an EKG equipment to terminal 30. Also, one or more clip type electrodes 40 can make common electrical contact between monitoring equipment and terminal 30, through contact layer 20, while not interfering with the connection at receiver 36.

The materials of construction, type of construction and operating enablements of the present apparatus will be understood from the incorporated reference, U.S. Pat. No. 5,626,135. However, the present apparatus clearly improves on the embodiments taught in this reference by enabling rotation of the contact layer 20 while assuring good electrical continuity with terminal 30.

The enablements described in detail above are considered novel over the prior art of record and are considered critical to the operation of at least one aspect of the apparatus and its method of use and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that each named inventor believes that the claimed subject matter is what is intended to be patented.

What is claimed is:

1. A medical electrode apparatus for simultaneous use with more than one electrical instrument, the apparatus comprising: an insulating adhesive layer and an electrically conducting contact layer secured in a frictionally abutting relationship on an electrical terminal such that the contact layer is rotatable about the terminal; the contact layer providing an electrically conductive surface in sliding contact with a flange of the terminal; the terminal providing a base portion positioned for electrical contact with a skin surface when the adhesive layer is adhered to the skin surface; the contact layer and the adhesive layer compressed between the flange and the base portion of the terminal such that a resilient force of the adhesive layer applies a selected contact force between the flange and the contact layer.

2. The apparatus of claim 1 wherein the contact layer is formed with a plurality of contact tabs; the contact tabs being free of the adhesive layer.

3. The apparatus of claim 1 wherein the adhesive layer is formed from a flexible sheet stock of foam material having a peripheral adhesive coating on one side thereof.

4. The apparatus of claim 1 wherein the contact layer is formed from a flexible, stiff, sheet stock.

5. The apparatus of claim 4 wherein the flexible sheet stock is at least one of: paper, cardboard, and plastic.

6. The apparatus of claim 4 wherein the conductive surface is at least one of: an adhering metallized layer, a bonded metal foil layer, and a metal electrodeposited layer.

7. The apparatus of claim 1 wherein to contact layer provides a central clearance hole with radial cuts for assembly of the contact layer onto the terminal.

8. The apparatus of claim 1 wherein the terminal provides a central male receiver for a snap-on terminal.

* * * * *